US010130295B2

(12) United States Patent
Smith

(10) Patent No.: US 10,130,295 B2
(45) Date of Patent: Nov. 20, 2018

(54) METHOD FOR THE DETECTION AND STAGING OF LIVER FIBROSIS FROM IMAGE ACQUIRED DATA

(71) Applicant: UNIVERSITY OF MISSISSIPPI MEDICAL CENTER, Jackson, MS (US)

(72) Inventor: Andrew Smith, Ridgeland, MS (US)

(73) Assignee: UNIVERSITY OF MISSISSIPPI MEDICAL CENTER, Jackson, MS (US)

( * ) Notice: Subject to any disclaimer, the term of this patent is extended or adjusted under 35 U.S.C. 154(b) by 0 days.

(21) Appl. No.: 14/595,122

(22) Filed: Jan. 12, 2015

(65) Prior Publication Data

US 2015/0148658 A1 May 28, 2015

Related U.S. Application Data

(63) Continuation of application No. PCT/US2013/050139, filed on Jul. 11, 2013.
(Continued)

(51) Int. Cl.
*A61B 5/00* (2006.01)
*G06T 7/00* (2017.01)
(Continued)

(52) U.S. Cl.
CPC ............ *A61B 5/4244* (2013.01); *A61B 5/055* (2013.01); *A61B 8/485* (2013.01); *G06T 7/0012* (2013.01);
(Continued)

(58) Field of Classification Search
CPC ....... A61B 8/085; A61B 5/4244; A61B 8/485; A61B 5/055; A61B 6/032; A61B 8/08; G06T 7/0012; G06T 2207/20036; G06T 2207/20076; G06T 2207/10081; G06T 2207/10088; G06T 2207/30056;
(Continued)

(56) References Cited

U.S. PATENT DOCUMENTS 9,265,479 B2     2/2016  Yao et al.
2011/0172533 A1*  7/2011  Yao .......................... A61B 8/08
                                                            600/443
(Continued)

FOREIGN PATENT DOCUMENTS

JP    2005-319080    11/2005
JP    2008-543748    12/2008
(Continued)

OTHER PUBLICATIONS

Computed Tomography of Hepatic Morphologic Changes in Cirrhosis of the Liver by Torres et al. Pub. Journal of Computer Assisted Tomography. 10(1):47-50, Jan./Feb. 1986.*
(Continued)

*Primary Examiner* — Katherine Fernandez
*Assistant Examiner* — Michael Kellogg
(74) *Attorney, Agent, or Firm* — Workman Nydegger

(57) ABSTRACT

This invention relates to methods for ascertaining at least one of liver fibrosis or cirrhosis in a subject, by processing of one or more medical images of the liver, using a computing machine, to quantify nodularity of the surface of the liver and calculate a liver surface nodularity score.

20 Claims, 4 Drawing Sheets

Related U.S. Application Data

(60) Provisional application No. 61/670,499, filed on Jul. 11, 2012.

(51) Int. Cl.

| | | |
|---|---|---|
| *A61B 5/055* | (2006.01) | |
| *A61B 8/08* | (2006.01) | |
| *G06F 19/00* | (2018.01) | |
| *A61B 6/03* | (2006.01) | |
| *G16H 50/20* | (2018.01) | |

(52) U.S. Cl.
CPC .............. *A61B 6/032* (2013.01); *A61B 8/08* (2013.01); *A61B 8/085* (2013.01); *G06F 19/321* (2013.01); *G06T 2207/10081* (2013.01); *G06T 2207/10088* (2013.01); *G06T 2207/10132* (2013.01); *G06T 2207/20036* (2013.01); *G06T 2207/20076* (2013.01); *G06T 2207/30056* (2013.01); *G16H 50/20* (2018.01)

(58) Field of Classification Search
CPC ......... G06T 2207/10132; G06F 19/345; G06F 19/321; G16H 50/20
See application file for complete search history.

(56) References Cited

U.S. PATENT DOCUMENTS

| | | | |
|---|---|---|---|
| 2011/0263443 A1* | 10/2011 | Hess | G01N 33/6863 506/7 |
| 2012/0010824 A1 | 1/2012 | Cales | |
| 2012/0133663 A1 | 5/2012 | Tanigawa | |
| 2013/0116564 A1 | 5/2013 | Katsuyama | |
| 2014/0005500 A1* | 1/2014 | Cales | A61B 5/4842 600/301 |
| 2014/0330106 A1* | 11/2014 | Banerjee | G01R 33/4828 600/410 |

FOREIGN PATENT DOCUMENTS

| | | |
|---|---|---|
| JP | 2011-143062 | 7/2011 |
| JP | 2012-115383 | 6/2012 |
| WO | 1998024065 | 6/1998 |
| WO | WO20060132460 | 12/2006 |
| WO | 2011083789 | 7/2011 |
| WO | 2011123068 | 10/2011 |
| WO | WO20120002421 | 1/2012 |
| WO | 2012022939 | 2/2012 |
| WO | 2014201052 | 12/2014 |

OTHER PUBLICATIONS

Diagnosis Performance of Different MR Imaging Signs of Cirrhosis: the Caudate to Right Lobe Ratio, the Posterior Right Hepatic Notch, and the Expanded Gallbladder Fossa by Bolog et al. Pub. Current health sciences journal vol. 35, No. 1, 2009.*
Noninvasive Tests for Hepatic Fibrosis by Aetna Pub. online Aug. 13, 2004 at http://www.aetna.com/cpb/medical/data/600_699/0690.html.*
Diagnosis and Quantification of Fibrosis by Manning et al Pub. Gastroenterology 2008; 134: pp. 1670-1681.*
Estimation of Stage-Specific Fibrosis Progression Rates in Chronic Hepatitis C Virus Infection: A Meta-Analysis and Meta-Regression by Thein et al. Pub. J. Hepatology, vol. 48 No. 2, 2008 pp. 418-431.*
Hepatic morphologic changes in cirrhosis: MR imaging findings by Ito et al. pub. Abdom Imaging 25:456-461 (2000) DOI: 10.1007/s002610000013.*
Diagnosis of Cirrhosis by Spiral Computed Tomography: A Case-Control Study With Feature Analysis and Assessment of Interobserver Agreement by Keed et al. pub. J Comput Assist Tomogr. Mar.-Apr. 2008; 32(2): 198-203. doi: 10.1097/RCT.0b013e31815ea857.*
Viral-Induced Cirrhosis: Grading of Severity Using MR Imaging by Ito et al. pub. AJR1999;173:591-596 0361-803X/99/1733-591.*
Edge enhancement by Wikipedia pub. online on May 26, 2012 at https://en.wikipedia.org/w/index.php?title=Edge_enhancement&oldid=494404243.*
Unsharp masking by Wikipedia pub. online on Jun. 15, 2012 at https://en.wikipedia.org/w/index.php?title=Unsharp_masking&oldid=497718852.*
Computer-Aided Diagnosis of Hepatic Fibrosis: Preliminary Evaluation of MRI Texture Analysis Using the Finite Difference Method and an Artificial Neural Network by Kato et al. pub. AJR:189, Jul. 2007 pp. 117-122.*
Kim, et al.; Acoustic radiation force impulse elastography for chronic liver disease: comparison with ultrasound-based scores of experienced radiologists, child-pugh scores and liver function tests; Ultrasound in Med. and Biol; vol. 36, No. 10; 2010; pp. 1637-1643.
Smith, et al., Development of post-processing software to diagnose and stage HCV-induced cirrhosis by quantification of liver surface nodularity on routine CT images; Society of Computed Body Tomography and Magnetic Resonance (SCBT-MR) 2013 Annual Meeting—New Orleans, LA; Oct. 14, 2014; Abstract.
Smith, et al., Introduction of a new biomarker—A combination of FIB-4 score and liver surface nodularity score measured on routine CT images accurately stages HCV-induced chronic liver disease; American Roentgen Ray Society 2014 Annual Meeting—San Diego, CA; May 9, 2014; Abstract.
Smith, et al., Predicting liver-related events in patients with cirrhosis using liver surface nodularity measurements from routine CT images; Society of Computed Body Tomography and Magnetic Resonance (SCBT-MR) 2014 Annual Meeting—New Orleans, LA; Sep. 30, 2014; Abstract.
Smith, et al., Liver surface nodularity scores derived from CT images predict cirrhosis decompensation and death; Society of Abdominal Radiology Annual Meeting—San Diego, CA; Mar. 22, 2015.
Nguyen D and Talwalkar JA. Noninvasive assessment of liver fibrosis. Hepatology 2011; 53:2107-2110.
Lee HS, Kim JK, Han EJ, et al. Prediction of compensated liver cirrhosis by ultrasonography and routine blood tests in patients with chronic viral hepatitis. Korean J Hepatol 2010; 16:369-75.
Choong CC, Venkatesh SK, Siew EP. Accuracy of routine clinical ultrasound for staging of liver fibrosis. J Clin Imaging Sci 2012; 2:58.
Moon KM, Baik SK, Choi E, et al. Ultrasonographic scoring system score versus liver stiffness measurement in prediction of cirrhosis. Clin Mol Hepatol 2013; 19:389-98.
Ferral H, Male R, Cardiel M, et al. Cirrhosis: Diagnosis by liver surface analysis with high-frequency ultrasound. Abdom Imaging. 1992; 17:74-78.
Kudo M, Zheng RQ, Kim SR, et al. Diagnostic accuracy of imaging for liver cirrhosis compared to histologically proven liver cirrhosis. Intervirology 2008; 51:17-26.
Saygili OB, Tarhan NC, Yildirim T, et al. Value of computed tomography and magnetic resonance imaging for assessing severity of liver cirrhosis secondary to viral hepatitis. Eur J Radiology 2005; 54:400-407.
Castera L. Noninvasive methods to assess liver disease in patients with hepatitis B or C. Gastroenterol 2012; 142:1293-1302.
Rockey D and Bissell DM. Noninvasive measures of liver fibrosis. Hepatology 2006; 43:S113-S120.

* cited by examiner

A.

B.

METHOD FOR THE DETECTION AND STAGING OF LIVER FIBROSIS FROM IMAGE ACQUIRED DATA

PRIOR APPLICATIONS

This application is a continuation of International Application No. PCT/US2013/050139, filed Jul. 11, 2013, which claims the benefit of Provisional Patent Application No. 61/670,499, filed Jun. 1, 2012, the contents of which are incorporated herein by reference.

BACKGROUND OF THE INVENTION

Examples of the methods described herein are designed to screen for, diagnose, stage severity of, and evaluate response to therapy of liver fibrosis and/or cirrhosis in order to reduce or obviate the need for a liver biopsy in an individual with unsuspected or suspected chronic liver disease.

Liver fibrosis is a condition of liver inflammation and fibrotic scarring that may regress, stabilize or progress to cirrhosis under different treatment conditions. Cirrhosis is a consequence of chronic progressive liver fibrosis and is characterized by replacement of liver tissue by fibrotic scar tissue and regenerative nodules. Cirrhosis may decompensate and lead to liver failure, ascites, varices, hepatocellular carcinoma, hepatic encephalopathy, and death.

Because compensated cirrhosis is asymptomatic, cirrhosis is often undiagnosed, and it is estimated that up to 1% of the U.S. population (3.1 million individuals) may have cirrhosis. Cirrhosis is the eleventh-leading cause of death and responsible for 25,000 deaths in the U.S. each year. Similar numbers have been reported in Europe, and higher numbers are expected in Asia and Africa, where hepatitis C virus (HCV) and hepatitis B virus (HBV) are more common. Most forms of cirrhosis are progressive and lead to the aforementioned complications and death in the absence of a liver transplant, which is an invasive, risky, and expensive.

Cirrhosis is frequently unsuspected and indolent until decompensation, when complications of liver disease are clinically evident. Patients with decompensated cirrhosis present with symptoms of jaundice, ascites, bleeding varices, and/or hepatic encephalopathy, and the diagnosis is made by clinical presentation, medical history, blood laboratory tests, and imaging findings. Occasionally, a liver biopsy is needed to diagnose decompensated cirrhosis. Compensated cirrhosis however is asymptomatic, and diagnosis is typically initiated when an incidental screening test such as liver transaminases or radiologic findings suggest liver disease, and the patients undergo clinical evaluation and liver biopsy.

The most common causes of liver fibrosis and cirrhosis are HCV infection, non-alcoholic fatty liver disease (NAFLD), and alcoholic liver disease, though there are numerous other causes. Currently, the most common cause of liver fibrosis and cirrhosis is HCV infection, which is associated with 15,000 deaths in the U.S. each year. The natural course of HCV infection is variable, though up to 20% of individuals progress to cirrhosis. There is a low risk of progression to severe fibrosis or cirrhosis over 10 to 20 years in patients with HCV and no fibrosis or inflammation. In patients with HCV and bridging fibrosis, there is high risk of progression to cirrhosis.

Up to 30% of the adult U.S. population has NAFLD, which includes simple steatosis, steatosis with inflammation, non-alcoholic steatohepatitis (NASH), and NASH cirrhosis. Because of an association with obesity, which is increasing in incidence, NAFLD and NASH are increasing in incidence. NASH is present in as many as 40% to 75% of patients with NAFLD and elevated transaminases, and many patients with NAFLD and normal transaminases have NASH. NASH has the potential to progress to cirrhosis in 10 to 20% of individuals and is predicted to be the number one cause of cirrhosis in the next decade. Considering the high prevalence of NAFLD in the general population, and that any patient with NAFLD may have NASH, it is estimated that nearly one quarter of the Western population needs screening for NASH (equivalent to 775,000 individuals in the U.S.).

Treatment of liver fibrosis and cirrhosis is aimed at stopping or delaying progression to cirrhosis to reduce or delay complications of decompensated cirrhosis. Not all patients with HCV infection or NAFLD develop liver fibrosis or cirrhosis, and cirrhosis is difficult to diagnose unless it has decompensated and lead to clinically detectable signs of portal hypertension such as ascites or symptomatic varices. By comparison, liver fibrosis and compensated cirrhosis are asymptomatic and cannot be detected without screening measures, even in patients with HCV infection or known NAFLD.

The traditional method for diagnosis of liver fibrosis and cirrhosis of any cause is by random liver biopsy. Staging of liver fibrosis by biopsy in patients with HCV infection is frequently accomplished by the METAVIR system, which categorizes disease into 5 groups (F0 to F4) based on subjective assessment of a histopathology biopsy sample by a hepatopathologist. A similar histological classification method of staging liver fibrosis (F0-F4) is used in NAFLD. Biopsy is a suboptimal clinical tool because of sampling error, subjective qualitative assessment of biopsy samples and classification into categories instead of continuous units, intraobserver and interobserver variation in biopsy result reporting, high cost, relatively long procedure time (especially if conscious sedation is used), low throughput, and risks of pain, bleeding, infection and rarely death. Furthermore, biopsy results are not able to stage the severity of cirrhosis. Staging of cirrhosis is important for prediction and treatment of complications and allocation of liver transplants. Cirrhosis staging is performed via a combination of clinical and laboratory factors as done by Child-Pugh classification or Model for End Stage Liver Disease (MELD) score. The shortcomings of liver biopsy have spurred interest in development of noninvasive tests as a potential alternative to biopsy.

Routine qualitative assessment of medical imaging by ultrasound, computerized tomography (CT), and magnetic resonance imaging (MRI) is generally considered insensitive for detection of cirrhosis and inaccurate for staging the severity of cirrhosis. However, the specificity of subjective medical imaging assessment for extreme liver surface nodularity and varices is high in end-stage cirrhosis. The current role of medical imaging is for the detection of complications of cirrhosis including detection of varices, ascites, hepatocellular carcinoma, and hepatic or portal venous thrombosis. Routine medical imaging is not used in clinical practice to screen for, diagnose, stage severity of, or evaluate response to therapy of liver fibrosis or early stage (compensated) cirrhosis.

Two prominent methods for noninvasively staging liver fibrosis include laboratory tests (predominantly blood tests) and tests that measure the physical stiffness of the liver. A variety of blood tests have moderate to high accuracy (area under the receiver-operating characteristic curve [ROC] median range of 0.59 to 0.86) for differentiating normal and inflamed livers from liver fibrosis and cirrhosis and moderate to high accuracy (ROC median range 0.65 to 0.91) for differentiating noncirrhotic from cirrhotic livers, in individuals HCV infection. Similar accuracies with blood tests have been found in patients with NAFLD.

Increased liver stiffness has been associated with increased liver fibrosis and cirrhosis. A number of techniques have been proposed that provide quantitative physical measures of liver stiffness from imaging or clinical measurement devices. Specifically liver stiffness has been measured by transient elastography (TE), ultrasound shear wave elastography (SWE), ultrasound acoustic radiation force elastography (ARFI), ultrasound strain (static or compression) elastography, magnetic resonance elastography (MRE), and other methods. Each of these methods has moderate to high accuracy for differentiating mild liver fibrosis from severe liver fibrosis and cirrhosis and for differentiating noncirrhotic livers from cirrhotic livers. Problems with transient elastography and ultrasound elastography techniques are limited applicability in moderate to severely obese patients, suboptimal reproducibility of results related to various factors (operator experience, patient body habitus, presence or absence of ascites, etc.), inability to assess the stiffness of the entire liver or central regions of the liver, requirement of a dedicated device to make the measurements, inability to make stiffness measurements on ultrasound images from prior studies without the dedicated device, lack of standardization of methods among different vendors, and false positive cases from other causes of liver stiffness (e.g. liver congestion from cardiac disease). The main problems with MRE are limited applicability in moderate to severely obese patients or in patients with iron overload, requirement of a dedicated device to make the measurements, inability to make stiffness measurements on magnetic resonance images from prior studies without the dedicated device, lack of portability and requirement for a MRI facility, time consuming with low throughput, inability to standardize the technique across multiple scanners and vendors, frequency of individuals with contraindications to MRE (e.g. individuals with pacemakers or severe claustrophobia), high cost, artifacts and failed MRE examinations, and false positive cases from other causes of liver stiffness.

Assessment of segmental liver volume and subjective assessment of liver parenchymal nodularity on medical images for features of severe liver fibrosis and cirrhosis have been evaluated, though overall accuracy of these methods has been poor (<67%), despite the use of imaging experts as readers. The poor accuracy can be attributed to poor interobserver agreement, particularly in the evaluation for the presence or absence of liver parenchymal nodularity by MRI (overall kappa 0.33 between 3 readers). Similar poor accuracy (45%) has been seen with subjective analysis of liver surface nodularity by high frequency ultrasound. Accuracy for diagnosing cirrhosis by subjective qualitative nodularity assessment on CT images was higher at ROC of 0.92, though interobserver agreement was unsatisfactory for routine clinical practice (kappa 0.75). Even with medical image interpretation by experts, these techniques have not been accepted as having high enough accuracy or reproducibility to be incorporated into clinical practice, particularly since expert readers are not universally available at all points of care for patients with chronic liver disease.

After >25 years of medical imaging of liver disease by CT, MRI and ultrasound, no one has proposed or invented a quantitative method for measuring liver surface nodularity on medical images, until this patent application. Previous methods have all been qualitative, not quantitative, binary assessments for the presence or absence of liver surface nodularity as interpreted by an expert in interpretation of medical images of the liver.

Thus, the present invention meets a long-felt need not accomplished by existing techniques and the prior art.

SUMMARY OF THE INVENTION

The methods described herein are designed to at least one of screen for, diagnose, stage severity of, and evaluate response to therapy of liver fibrosis and/or cirrhosis in order to reduce or obviate the need for a liver biopsy in an individual with unsuspected or suspected chronic liver disease. The methods are intended for use in interpretation of medical images of the liver by radiologists and by clinicians skilled in the art of diagnosis and/or treatment of liver fibrosis and cirrhosis.

One embodiment of the present invention is method for ascertaining at least one of liver fibrosis or cirrhosis in a subject, said method comprising: processing of one or more medical images of the liver, using a computing machine, to quantify nodularity of the surface of the liver and calculate a liver surface nodularity score.

In embodiment, the method further comprising processing the liver surface nodularity score as a metric, wherein the process step considers at least one of an individual's computed tomography (CT), magnetic resonance (MR), or ultrasound grayscale medical images.

In another embodiment of the present invention, the liver surface nodularity score is expressed in continuous units, with a higher liver surface nodularity score being associated with a higher stage of liver fibrosis or cirrhosis.

Another embodiment of the present invention further comprising generating the liver surface nodularity score with a computer machine using a software algorithm that performs detection and enhancement of the medical images for a section of liver boundary edges, and liver surface nodularity measurement from the detected liver boundary.

Another embodiment further comprising generating the liver surface nodularity score with a computer machine by considering the divergence between a detected section of liver boundary and a smoothed spline that mimics the course of a section of smooth liver surface.

Another method further comprising the step of processing at least one of said medical images to acquire at least one measurement of liver volume and mathematically combining said measurement with said liver surface nodularity score to arrive at a clinically-predictive algorithm to stage liver fibrosis and/or cirrhosis.

Another embodiment comprises the step of processing at least one of said medical images to acquire at least one measurement of liver morphology and mathematically combining said measurement with said liver surface nodularity score to arrive at a component clinically-predictive algorithm to stage liver fibrosis and/or cirrhosis.

Another embodiment comprises the step of identifying varices on medical images or by endoscopy report and using the presence of varices to diagnose cirrhosis with portal hypertension.

Another embodiment comprises obtaining and considering at least one of an age of the liver, a body mass index of a body to which the liver belongs, a blood laboratory test result, a urine laboratory test result, or a salivary laboratory test result, or any combination thereof; and mathematically combining said consideration with said liver surface nodularity score to arrive at a component clinically-predictive algorithm to stage liver fibrosis and/or cirrhosis.

Another embodiment further comprises the step of obtaining and considering at least one of a blood laboratory test result, and mathematically combining said result with said liver surface nodularity score to arrive at a component clinically-predictive algorithm to stage liver fibrosis and/or cirrhosis. Other possible test results include, for example, at least one of a urine laboratory test result, salivary laboratory test result, a platelet count, an albumin level, an aspartate aminotransferase (AST) level, an alanine aminotransferase (ALT) level, a gamma glutamyltransferase (GGT) level, a prothrombin time and international normalization ratio (INR) level, a partial thromboplastin time (PTT), an alkaline phosphatase level, a bilirubin level, a serum viral level or titer, an alpha-fetoprotein (AFP) level, a total cholesterol level, a LDH cholesterol level, a HDL cholesterol level, a triglyceride level, an alpha-2-microglobulin level, a haptoglobin level, an apolipoprotein A1 level, a hyaluronic acid level, an amino-terminal propeptide level, a tissue inhibitor of metalloproteinase level, or any combination thereof Another embodiment further comprising the step of using at least one of an imaging measurement device or a clinical measurement device to obtain a physical measure of liver stiffness, from one of an imaging measurement device or a clinical measurement device; and mathematically combining the result of said measurement with said liver surface nodularity score to arrive at a component clinically-predictive algorithm to stage liver fibrosis and/or cirrhosis. The physical measure of liver stiffness step may include measuring a quantitative liver stiffness value by at least one of transient elastography (TE), ultrasound shear wave elastography (SWE), ultrasound acoustic radiation force elastography (ARFI), ultrasound strain (static or compression) elastography, or magnetic resonance elastography (MRE).

In another embodiment the step of processing of one or more medical images of the liver may include measuring liver surface nodularity caused by irregular outward and inward projections of the liver surface that are associated with at least one of the presence of inflammation, fibrotic tissue, scarring, or regenerative nodules.

It is understood that any embodiment, or any combination of embodiments can be combined with the nodularity score to arrive at a component clinically-predictive algorithm to stage liver fibrosis and/or cirrhosis. For example, the step of using at least one of an imaging measurement device or a clinical measurement device to obtain a physical measure of liver stiffness, from one of an imaging measurement device or a clinical measurement device; and mathematically combining the result of said measurement with said liver surface nodularity score can be combined with the step of obtaining a physical measure of liver stiffness to arrive at a component clinically-predictive algorithm to stage liver fibrosis and/or cirrhosis.

One embodiment of the present invention is a method to quantify liver surface nodularity on an individual's routine medical images (CT, MRI or ultrasound) using a software algorithm that leads to a liver surface nodularity score in continuous units. Another embodiment of the present invention is an extension of this method so that the continuous units can be categorized or used to develop a threshold value that is clinically important.

One embodiment of the present invention is the establishment of a liver surface nodularity score that can be used to screen for, diagnose, stage severity of, and evaluate response to therapy of cirrhosis. When the liver surface nodularity score is used in combination with at least one of liver morphometric measures, measures of portal hypertension, and measures of laboratory factors, or any combination thereof, one can screen for, diagnose, stage severity of, and evaluate response to therapy of both liver fibrosis and cirrhosis. Additionally, one can mathematically combine the liver surface nodularity score with quantitative methods for measuring liver stiffness to provide an alternative method to screen for, diagnose, stage severity of, and evaluate response to therapy of both liver fibrosis and cirrhosis. The mathematical combination of the liver surface nodularity score with other aforementioned variables and factors can be accomplished in multiple forms and variations, and it is therefore the concept of a mathematical combination that is unique to this patent application, not any one particular mathematical formula.

For example, one embodiment of the present invention is a combination of the liver surface nodularity score with a segmental liver volume (e.g. left lateral segment to total liver volume ratio), the presence or absence of varices (a sign of portal hypertension), and a blood platelet level.

The advantages of the methods of the present invention are numerous, and include at least the following: noninvasive; provides a quantitative continuous numeric value for the degree of liver surface nodularity that correlates with the severity of liver fibrosis and/or cirrhosis; utilizes highly standardized quantitative methods of image acquisition and processing; short scan time with rapid, reliable and quantitative analysis of the medical images; ability to use routine medical images from CT, MRI or ultrasound, which are widely available at medical centers that treat patients with chronic liver disease; multiple imaging measurements are possible on the same individual's medical images, providing a sample of the entire liver surface; ability to process previously gathered medical images as well as newly acquired images; capability for high throughput; few contraindications to image acquisition and liver surface nodularity measurements; and low cost for acquiring images and low cost for liver surface nodularity measurements.

DETAILED DESCRIPTION OF THE INVENTION

Figure 1:
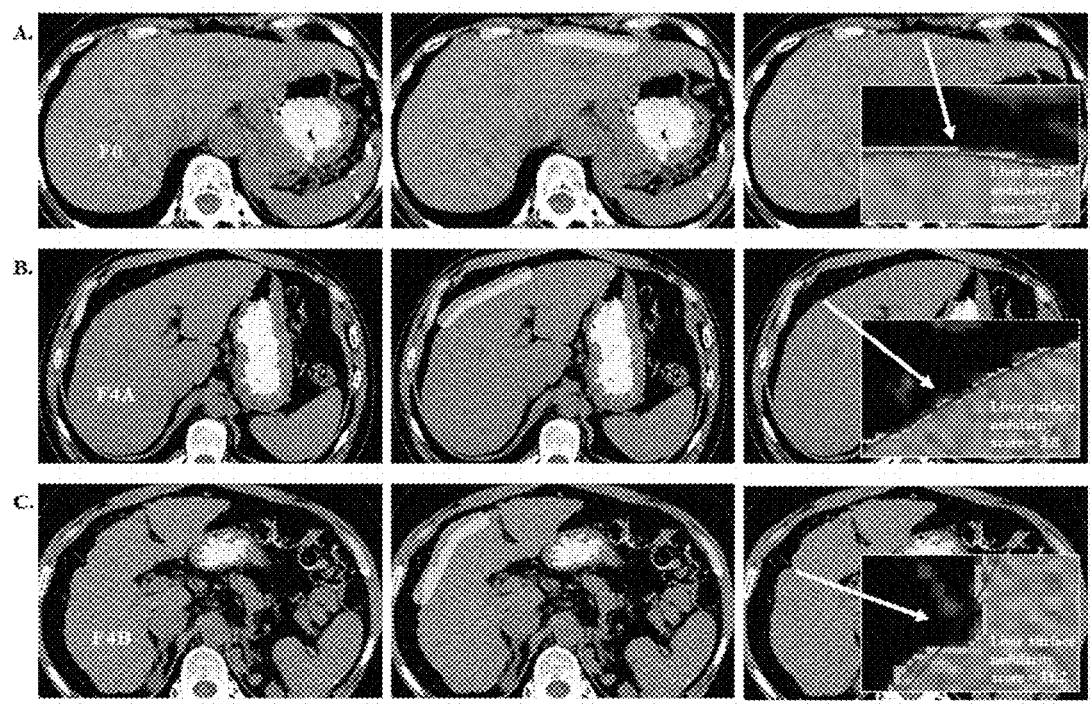
FIG. 1 shows how noncontrast computed tomography images from three individuals with different stages of liver disease can be displayed and analyzed by the liver surface nodularity software algorithm.

The present invention can be understood more readily by reference to the following detailed description of the invention and the Examples included therein.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which need to be independently confirmed.

All publications Although specific terms are employed herein, they are used in a generic and descriptive sense only and not for purposes of limitation. All terms, including technical and scientific terms, as used herein, have the same meaning as commonly understood by one of ordinary skill in the art to which this invention belongs unless a term has been otherwise defined. It will be further understood that terms, such as those defined in commonly used dictionaries, should be interpreted as having a meaning as commonly understood by a person having ordinary skill in the art to which this invention belongs. It will be further understood that terms, such as those defined in commonly used dictionaries, should be interpreted as having a meaning that is consistent with their meaning in the context of the relevant art and the present disclosure. Such commonly used terms will not be interpreted in an idealized or overly formal sense unless the disclosure herein expressly so defines otherwise.

As used in the specification and claims, the singular form "a", "an" and "the" include plural references unless the context clearly dictates otherwise. For example, the term "a measurement" includes a plurality of separate measurements.

As used herein, the term "comprising" is intended to mean that the compositions or methods include the recited elements, but not excluding others.

As used herein, a "subject," "individual" or "patient" is used interchangeably herein, which refers to a vertebrate, preferably a mammal, more preferably a human. Mammals include, but are not limited to, murines, simians, humans, farm animals, sport animals, and pets.

The phrase "pathological liver condition" is used interchangeably with "liver disorder" or "liver disease" to indicate any structural and/or functional liver abnormalities. Non-limiting examples of pathological liver conditions contemplated by embodiments of the present invention are used interchangeably and include those conditions associated with liver fibrosis, liver cirrhosis, and other toxic liver damage.

As used herein, the term "liver fibrosis," refers to the presence of inflammation and scar tissue in the liver. The term "cirrhosis" refers to an advanced stage of liver fibrosis, defined by chronic progressive liver fibrosis characterized by replacement of liver tissue by fibrotic scar tissue and regenerative nodules. For purposes of this specification and claims, "cirrhosis" is considered to be a type of liver fibrosis, and is included within the meaning of the term "fibrosis" used herein.

As used herein, the term "morphology," refers to the 2-dimensional or 3-dimensional shape of the liver or a segment of the liver that is associated with changes of liver fibrosis and cirrhosis. For the purposes of this specification and claims, "morphology" may also refer to 2-dimensional or 3-dimensional changes in liver shape responsible for liver surface nodularity.

As used herein, the term "nodularity," refers to the outward projections and inward retractions and overall irregularity of the liver surface that are caused by regenerative nodules, fibrotic bands, and other morphologic alterations found in advanced liver fibrosis and cirrhosis.

As used herein, the term "liver boundary," refers to the outer surface or edge of the liver on medical images where the liver contacts adjacent structures including abdominal fat, ascites, the diaphragm, the abdominal wall musculature, and other adjacent organs and tissues.

As stated above, a method of the present invention is a method for ascertaining at least one of liver fibrosis or cirrhosis in a subject, said method comprising the step of processing of one or more medical images of the liver, using a computing machine, to quantify nodularity of the surface of the liver and calculate a liver surface nodularity score.

Medical images of the liver are obtained by imaging devices including computed tomography (CT), magnetic resonance imaging (MRI), or ultrasound scanners. The medical images are displayed in grayscale. A liver surface nodularity score can be generated from prospectively gathered medical images that are optimized for liver surface nodularity score quantification or from previously gathered medical images.

Examples of methods for quantifying the liver surface nodularity score from an individual's CT, MR, or ultrasound grayscale medical images of the present invention include those that can be divided into two steps: (a) liver boundary edge enhancement and detection, and (b) liver boundary nodularity quantification.

A software algorithm is used to view and enhance the medical images for liver boundary edge detection. An edge enhancement filter in combination with an optional denoising filter will optimize the grayscale images for liver boundary edge detection. The pixel intensities in the medical images are displayed for optimal edge detection by thresholding and windowing techniques to optimize contrast between the liver and adjacent structures (particularly abdominal fat and ascites).

Segmentation of the liver boundary edge can be performed using individual 2-dimensional (2D) images or using a 3-dimensional (3D) image reconstruction derived from 2D images. The liver edge, or surface, is defined as the outer margin of the liver that is in contact with abdominal fat, ascites, the diaphragm, the abdominal wall musculature, and other adjacent organs and tissues. The most useful portions of the liver surface for detection of fine liver surface nodularity are where the liver surface contacts abdominal fat or ascites, though larger liver surface nodularity can be detected at other interfaces, particularly the diaphragmatic and lung interface.

Image segmentation can be semi-automated by placement of a user-directed region-of-interest (ROI) or fully automated, with or without reference to an imaging atlas. Edge sensitivity, which determines how well "weak" edges are detected, is adjusted by the user or may be set at optimized parameters. After liver boundary edge detection, pixels are stitched together to form a line that runs along the surface of the liver; this line represents the "detected liver boundary". Different edge sensitivities are used to find an optimal detected liver boundary for quantification of the liver surface nodularity score.

The liver surface nodularity score is a measurement. The liver surface nodularity score is a continuous numeric value that provides a measurement of the outward projections, inward retractions and overall irregularity of the liver surface that are caused by regenerative nodules, fibrotic bands and other morphologic alterations found in liver fibrosis and cirrhosis. For an individual with a nodular liver surface, the greater the deviation of the outward projections and inward retractions are from an expected smooth liver surface and the greater the overall irregularity of the liver surface, the larger the liver surface nodularity score. Multiple locations are measured to ensure an adequate sampling of the liver surface nodularity, and this can be done manually by the user or by automated or semi-automated methods.

Once the detected liver boundary is established, a variety of measurements are performed. A spline (a polynomial smoothed curve) can be fit to the detected liver boundary line. Multiple different polynomials can be generated utilizing different contours that provide different abilities to measure fine or large liver surface nodularity. Alternatively or in addition, the overall bumpiness of the detected liver boundary can be directly quantified.

The distance between the detected liver boundary and spline is measured on a pixel-by-pixel basis. Larger distances between the detected liver boundary and spline correspond to larger liver surface nodularity scores. Highly irregular liver surface nodularity is associated with larger variations in distances between the detected liver boundary and the spline and increases the liver surface nodularity scores. Small differences between the detected liver boundary and spline are expected in individuals with a smooth liver surface.

In order to enhance detection of liver surface nodularity, the distances between the detected liver boundary and the spline are adjusted exponentially (e.g. squared), which emphasizes larger distances (and corresponding nodularity) and deemphasize smaller distances that can be found with smooth liver surfaces. Alternative mathematical adjustments (e.g. log transformation) may further enhance the liver surface nodularity score. A mean of these adjusted measurements corrects the measurements for the length of the ROI, such that values from short or long ROIs can be directly compared. A standard deviation of the adjusted measurements provides information both on overall maximal distances and the range of variance of the distances, and also corrects the measurements for the length of the ROI. Increased maximal distance between the lines is associated with large nodules, and increased variance in the distance measurements corresponds to increasing irregularity of the nodularity. In an alternate form, the area between the curves (ABC, area between the detected liver boundary and the spline) can be used as a measure of liver surface nodularity. The ABC is divided by the length of the detected liver boundary to correct for differences in length between different ROIs. The distances between the detected liver boundary and the spline and measurements of the overall surface irregularity and nodularity can be accomplished in a variety of mathematical forms to generate a liver surface nodularity score.

Another embodiment of the present invention is a method to screen for, diagnose the presence of, stage the severity of, and monitoring treatment response of liver fibrosis and cirrhosis in an individual by a mathematical combination of liver surface nodularity score with one or more of the following, or any combination thereof:
a.) liver morphometric measurements from medical images;
b.) the presence or absence and/or identification of signs of portal hypertension on medical images;
c.) an individual's age, and/or body mass index (BMI), and/or one or more blood, urine or salivary laboratory tests.

For example, the liver surface nodularity score may be combined with a segmental liver volume (e.g. left lateral segment to total liver volume ratio), the presence or absence of varices (a sign of portal hypertension), and a blood platelet level.

Liver morphometric measurements from medical images include measurements of total and/or segmental liver volume and/or measurements of total and/or segmental liver morphology on an individual's medical images. Total and segmental liver volume and liver morphology can be quantified in 3D reconstruction data sets derived from 2D grayscale medical. Liver morphology provides a measure of the liver shape, which can be by a variety of methods (elongation shape factor, compactness factor, waviness shape factor, etc.) that are in continuous units. Both liver volume and morphometry measures are associated with the stage of liver disease. The presence or absence and/or identification of signs of portal hypertension on medical images refer to identification and qualitative assessment of the amount of ascites present and/or the presence or absence of varices associated with portal hypertension. Varices and ascites are typically found only in patients with cirrhosis. An individual's age, BMI, and multiple blood, urine or salivary laboratory tests are associated with the severity of liver cirrhosis. Each of these variables and factors can be mathematically combined with the liver surface nodularity score to accurately screen for, diagnose, stage the severity of, and monitoring treatment response in an individual with unsuspected or suspected liver fibrosis or cirrhosis.

Another embodiment of the present invention is a method to screen for, diagnose the presence of, stage the severity of, and monitoring treatment response of liver fibrosis and cirrhosis in an individual by a mathematical combination of the liver surface nodularity score with a physical measure of liver stiffness from an imaging or clinical measurement device. The liver surface nodularity score would be measured as described above from grayscale medical images (CT, ultrasound, or MRI) and mathematically combined with a physical measure of liver stiffness from an imaging or clinical measurement device that quantitatively measures liver elasticity or stiffness by transient elastography (TE), ultrasound shear wave elastography (SWE), ultrasound acoustic radiation force elastography (ARFI), ultrasound strain (static or compression) elastography, magnetic resonance elastography (MRE), or another method. The liver surface nodularity score and liver stiffness measurements are in continuous units and can be combined mathematically by logistic regression or a polynomial.

The present invention has been described in terms of one or more preferred embodiments, and it should be appreciated that many equivalents, alternatives, variations, and modifications, aside from those expressly stated, are possible and within the scope of the invention. In particular, one of ordinary skill in the art would appreciate that the software algorithm for liver surface nodularity quantification can be written in various forms or alternatives that provide a quantitative measure of liver surface nodularity. Also, the precise mathematical combination of liver surface nodularity score with liver morphometric measurements from medical images, the presence or absence and/or identification of signs of portal hypertension on medical images, an individual's age, and/or body mass index, and/or one or more blood, urine or salivary laboratory tests, and with a physical measure of liver stiffness can be described in various forms or alternatives.

Example

The following examples are intended to be exemplary of embodiments of the present invention, and not to be construed as being limiting thereof.

One embodiment of the present invention is a software algorithm for quantification of liver surface nodularity on an individual's medical images (CT, MRI or ultrasound) leading to a liver surface nodularity score that can be used alone or in combination with other variables to screen for, diagnose, stage severity of, and evaluate response to therapy in individuals with unsuspected or suspected liver fibrosis and/or cirrhosis. The liver surface nodularity score can be mathematically combined with other variable as described to screen for, diagnose, stage severity of, and evaluate response to therapy in individuals with unsuspected or suspected liver fibrosis and/or cirrhosis. The mathematical combination improves the accuracy for identifying and differentiating lower stage liver fibrosis.

Figure 2:
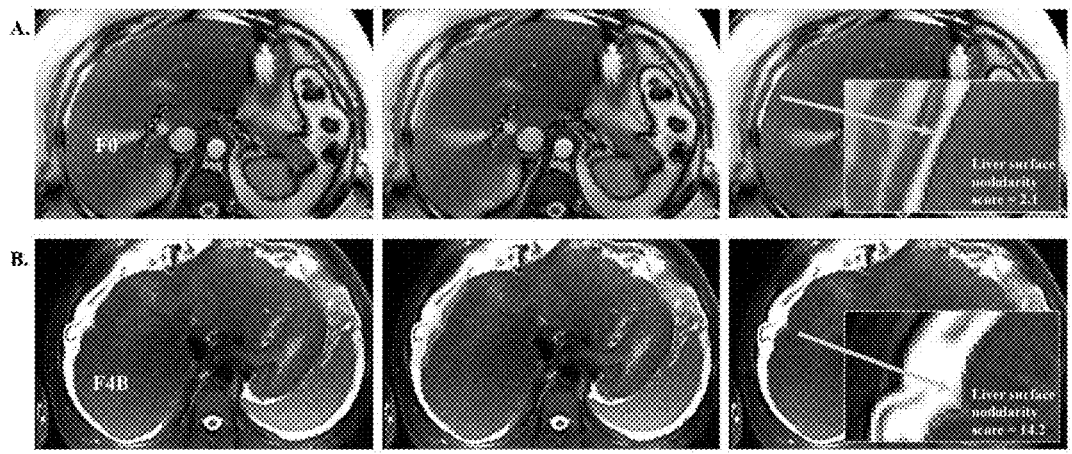
FIG. 2 shows how magnetic resonance images from two individuals with different stages of liver disease can be displayed and analyzed by the liver surface nodularity software algorithm.

In the present example, software algorithm opens and displays a stack of grayscale medical images of the liver in DICOM format (FIGS. 1 and 2). The user can scroll (or page) through the axial images of the liver and magnify and pan the images as desired to evaluate the liver surface.

The user can manually adjust the windowing of the images to enhance liver surface boundary detection. For CT images, the window width is preset at 225, and the window center is set to 50 for noncontrast liver CT images and 100 for portal-venous contrast-enhanced liver CT images. In an alternative form, the user measures the mean intensity of a portion of the liver, and the windowing is set in reference to those measurements.

The user scrolls through the images to look for sites where the liver boundary is against abdominal fat, since fat has substantially different signal intensity than the liver. On CT images, the attenuation of abdominal fat is −190 to −30 Hounsfield Units (HU), substantially lower in attenuation than the liver. It is the differential in pixel intensities between the liver and fat that forms the basis for liver edge detection, so both pixel intensity differences and windowing are important features for CT, MR and ultrasound images.

In one example, a user selects a circular ROI tool and paints along the liver surface (FIG. 1 middle column) on a single CT image (single slice). The anterior margin of the left lobe of the liver is the preferred site for placement of a user-defined ROI, though another site along the anterior or right lateral margin of the liver may be chosen if there is a greater degree of apparent liver surface nodularity elsewhere. The user is advised to choose a location where the liver boundary is against abdominal fat, though a location where the liver boundary is against ascites may be chosen if needed. The user is advised to avoid natural sharp edges and fissures and to avoid selection of the abdominal wall musculature when placing the ROI. Two different sized circular ROI tools are available. The present inventor has found that inadvertent selection of a sharp edge or fissure occasionally occurs at the beginning or end of the painted ROI, so these ends are automatically trimmed by 2 mm to reduce occurrence of this problem. The selected ROI serves as a mask, within which the liver boundary will be detected (FIG. 1 right column). In an alternative form, the segmentation of the liver surface boundary can be auto-segmented using preset rules governing ROI placement (e.g. where the liver boundary is against abdominal fat that measures at least 5 millimeter in thickness).

Figure 3:
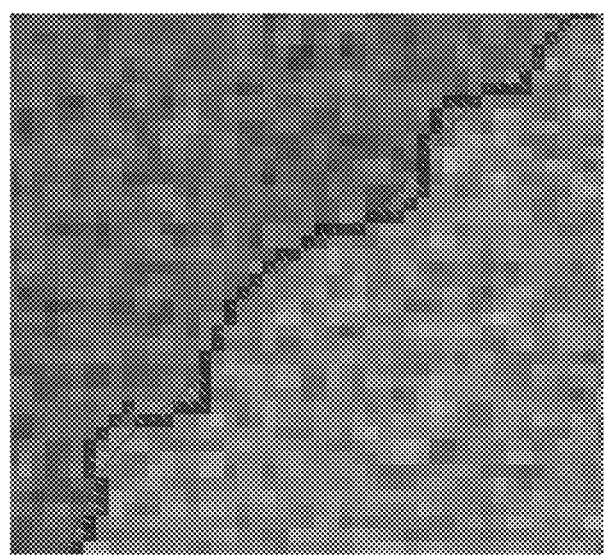
FIG. 3 shows how the distances between the detected liver boundary and spline can be measured for calculation of the liver surface nodularity score.

Edge sensitivity, which determines how well "weak" edges are detected, can be adjusted by the user. In the current version, 12 different edge sensitivities are chosen for each ROI. Within the user-selected ROI, the processing algorithm will automatically extract the liver boundary edge and analyze it to produce a set of metrics quantifying liver surface nodularity (FIG. 3). Liver surface nodularity measurements are made at all 12 sensitivities with images corresponding to the highest value displayed for confirmation and manual acceptance of the data by the user.

The following is an example of the liver boundary segmentation algorithm of the present invention:
1) An optional denoise feature is available to the user to reduce the influence of noisy pixels on the boundary in lower quality scans. In practice, this feature was available by button activation on the toolbar but not needed or used in our pilot study.
2) An edge detection filter is applied to the entire image, producing an edge mask where only pixels along the high-contrast interface between the liver and surrounding tissue are selected.
3) The resulting mask of step 2 is intersected with the user-defined painted ROI mask to exclude all regions except the desired boundary (FIG. 1 middle column).
4) A "skeletonization" filter is applied to reduce the remaining edge shapes to single-pixel connected line segments.
5) The disjointed line segments are "stitched" together, if necessary, and if their endpoints are sufficiently close.
6) All line segments are removed except the largest/longest line. The longest line is presumed to be the desired boundary edge and is termed the "detected liver boundary" (FIG. 1 right column).
7) The ends of the line are automatically trimmed by 2 mm as described above.
8) The length of the detected liver boundary line is measured and recorded.

The following is an example of the of the liver surface nodularity quantification algorithm of the present invention:
1) Using the detected liver boundary line as a reference, a spline is drawn within the ROI. The spline is a smoothed polynomial function (smooth line) that is fit to the detected liver boundary. The spline is designed to have a smoother (less nodular) course than the detected liver boundary, essentially mimicking what a smooth liver boundary should look like (FIG. 1 right column). The detected liver boundary will frequently intersect the spline at multiple points.
2) The contour fit parameters of the spline can be manually adjusted in the current version such that the spline may precisely match the detected liver boundary or significantly vary in distance from it by changing the contour parameters. An optimal contour fit was found at the 20 mm setting, providing a relatively smooth spline that allowed for optimal detection and quantification of a broad range of liver surface nodularities.
3) The shortest distances between the center of each of the detected liver boundary pixels and the spline are measured. In the current version of the software, the distances are squared to magnify the importance of larger variations. A mean and standard deviation of the squared distances within the ROI ($d_i$, i=1, . . . , n), are calculated and multiplied by 10 to derive the liver surface nodularity score by Mean Method or SD Method, respectively. The mathematical formulas defining the liver surface nodularity scores are as follows:

$$\text{Score based on Mean Method} = 10 \times \bar{d} = \frac{10}{n} \sum_{i=1}^{n} d_i$$

$$\text{Score based on SD Method} = 10 \sqrt{\frac{1}{n-1} \sum_{i=1}^{n} (d_i - \bar{d})^2}$$

4) The above distances are actually performed at all 12 edge detection sensitivity levels as described above. Each edge detection sensitivity results in different detected liver boundaries and corresponding splines. The detected liver boundary and corresponding spline at the sensitivity level with the highest value by the SD Method is depicted on the screen for review by the user (Max SD Method). The sensitivity level corresponding to the highest Mean Method is also recorded (Max Mean Method) but not visually displayed.

5) The detected liver boundary is displayed in green color, the spline is displayed in red color, and the length of the ROI and liver surface nodularity scores by Max SD Method and Max Mean Method are depicted in a box in the toolbar.

6) The user reviews the images (FIG. 1 right column), the ROI length, and the liver surface nodularity scores and confirms that the detected liver boundary and corresponding scores are appropriate. If appropriate, the user selects a button in the toolbar to save the liver surface nodularity measurements by both the Max SD Method and Max Mean Method. If the user does not think that the detected liver boundary or measurements appear appropriate or correct, the scores are discarded by scrolling to a different slice or by selecting the ROI tool, choosing another location for placement of a new ROI and calculation of new measurements.

7) Liver surface nodularity measurements are made 5 times for each patient by the user, with placement of 5 separate ROIs in 5 separate location. The median liver surface nodularity score (by Max SD Method or Max Mean Method) is recorded. In another form of the software algorithm, the user will make a minimum of 3 liver surface nodularity measurements, and additional measurements will be required until a sum of the length of the measured detected liver boundaries is greater than 10 cm.

FIG. 1 depicts noncontrast thin-slice liver CT images from three patients derived from the liver surface nodularity software algorithm. The top row (A) is from a patient with no liver disease (METAVIR stage F0), the middle row (B) is from a HCV-infected patient with advanced cirrhosis (METAVIR stage F4 and Child-Pugh classification A=F4A), and the bottom row (C) is from a HCV-infected patient with late stage cirrhosis (METAVIR stage F4 and Child-Pugh classification B=F4B). The images on the left are magnified views of the liver at preset window settings (center 50, width 225). The middle column images depict the user-guided selection of the liver surface ROI by a paint tool. The images in the right column show a 5 times magnified view of processed liver images depicting the detected liver boundary (thick dark gray pixilated line) and the spline (thin dark line). For the patient with F0 disease, the liver surface boundary and spline curves nearly overlap, and the liver surface nodularity score is low (2.0). For the patient with F4A disease, there is mild nodularity of the liver surface with intermittent separation of the liver surface boundary and spline curves and a corresponding elevated liver surface nodularity score (3.8). For the patient with F4B disease, there is severe nodularity of the liver surface with intermittent marked separation of the liver surface boundary and spline curves and a corresponding markedly elevated liver surface nodularity score (11.2). In this example, liver surface nodularity scores were a median of 5 measurements by Max SD Method.

FIG. 2 depicts a T2-weighted MR images from two patients derived from the liver surface nodularity software algorithm. The top row (A) is from a patient with no liver disease (METAVIR stage F0), and the bottom row (B) is from a HCV-infected patient with early cirrhosis (METAVIR stage F4 and Child-Pugh classification A=F4B). The images on the left are magnified views of the liver with windowing adjusted for optimal contrast between the liver and abdominal fat or ascites. The middle column images depict the user-guided selection of the liver surface ROI by a paint tool. The images in the right column show a 5 times magnified view of processed liver images depicting the detected liver boundary (large white pixilated line) and the spline (thin dark line). For the patient with F0 disease, the liver surface boundary and spline curves nearly overlap, and the liver surface nodularity score is low (2.1). For the patient with F4B disease, there is severe nodularity of the liver surface and a corresponding markedly elevated liver surface nodularity score (14.2). In this example, liver surface nodularity scores were a median of 5 measurements by Max SD Method.

FIG. 3 depicts a highly magnified non-enhanced thin-slice CT image of the liver surface that was selected by a user-defined region of interest (ROI). These images are from a HCV-infected patient with early cirrhosis (METAVIR stage F4 and Child-Pugh classification A). The liver is in the bottom right half of the images, and abdominal fat is in the top left half of the images. The liver surface as detected by the liver surface nodularity software is depicted by the dark line with large pixels and is termed the "detected liver boundary". A spline (thin dark line) is also depicted and is intentionally designed to have a smoother (less nodular) course than the detected liver boundary, essentially mimicking what a smooth liver boundary should look like for this patient. Thin white lines are seen between the detected liver boundary and the spline and represent the shortest distance between the center of the detected liver boundary pixels and the spline. The shortest distances between the center of each of the detected liver boundary pixels and the spline are measured. In the current version of the software, the distances are squared to magnify the importance of larger variations. A mean and standard deviation of the squared distances within the ROI ($d_i$, i=1, . . . , n), are calculated and multiplied by 10 to derive the liver surface nodularity score by Mean Method or SD Method, respectively.

The above techniques are applicable to MR images (FIG. 2) and ultrasound images by liver boundary edge enhancement and detection followed by liver boundary nodularity quantification using a software algorithm that provides a continuous numeric measurement value that corresponds to the amount and degree of liver surface nodularity on an individual's medical images.

As part of an institutional-review-board-approved retrospective pilot (proof of concept) study, electronic medical records were used to identify patients with routine liver CT imaging that included noncontrast and portal-venous-phase contrast-enhanced images with thin (0.6-2.0 mm) and thick (2.5-5.0 mm) slice axial images (NCCT-thin, NCCT-thick, CECT-thin, and CECT-thick imaging, respectively) between Jan. 1, 2006 and Mar. 3, 2011. Liver biopsy specimens from patients with HCV infection obtained <1 year from CT imaging (N=31) were read for METAVIR scoring by an expert hepatopathologist. Patients with normal livers but no biopsy (N=30) were assigned a score of F0. Patients clinically managed for HCV-induced cirrhosis but no biopsy (N=35) were assigned a score of F4. Child-Pugh scoring was used to group biopsy-proven and clinical cirrhosis (F4) severity as A, B, or C (N=56). The following blood laboratory levels within 6 months of CT imaging were recorded including the following: AST, ALT, total bilirubin, albumin, INR, platelets, and creatinine.

Using a version of the liver surface nodularity software algorithm, five measurements from each CT study (NCCT-thin, NCCT-thick, CECT-thin, and CECT-thick) were made by a fellowship trained body-imaging radiologist who was blinded to disease status. The user visually inspected the images at preset window settings and chose a ROI along the anterior margin of the left lobe of the liver that had the most visible surface nodularity and where the liver margin was against abdominal fat. If no measurements were possible in this region or there was obviously greater liver surface nodularity elsewhere, the anterior or right lateral margin of the liver was chosen for ROI placement. Natural sharp edges and fissures (particularly the fissure for the falciform ligament) and the abdominal wall musculature were avoided when placing the ROI. A total of 5 measurements were made, and the median liver surface nodularity scores by Max Mean Method and Max SD Method were recorded.

The same reader also measured total liver volume (TLV) and left lateral segment volume (LLSV) and looked for the presence or absence of portal venous varices on each imaging series. The LLSV to TLV ratio (LLSV:TLV ratio) was calculated.

The area under the ROC curve (AUC) was used to evaluate the accuracy of the nodularity score for differentiating cirrhotic from non-cirrhotic livers. Logistic regression analysis was conducted to assess the joint effect of liver surface nodularity score, liver imaging and laboratory variables on the stage of liver fibrosis and cirrhosis. Model building was performed for three sets of staging, F2-F4C versus F0-F1, F3-F4C versus F0-F2, and F4A-F4C versus F0-F3. We considered the following variables in multivariate analysis: liver volume measurements (TLV, LLSV, LLSV:TLV ratio), AST, ALT, total bilirubin, albumin, INR, platelets, creatinine, Child-Pugh score, and MELD score. If the p-value of a variable reached 5% significance level in any logistic regression models, the variable was determined as significant and kept in the final models.

Figure 4:
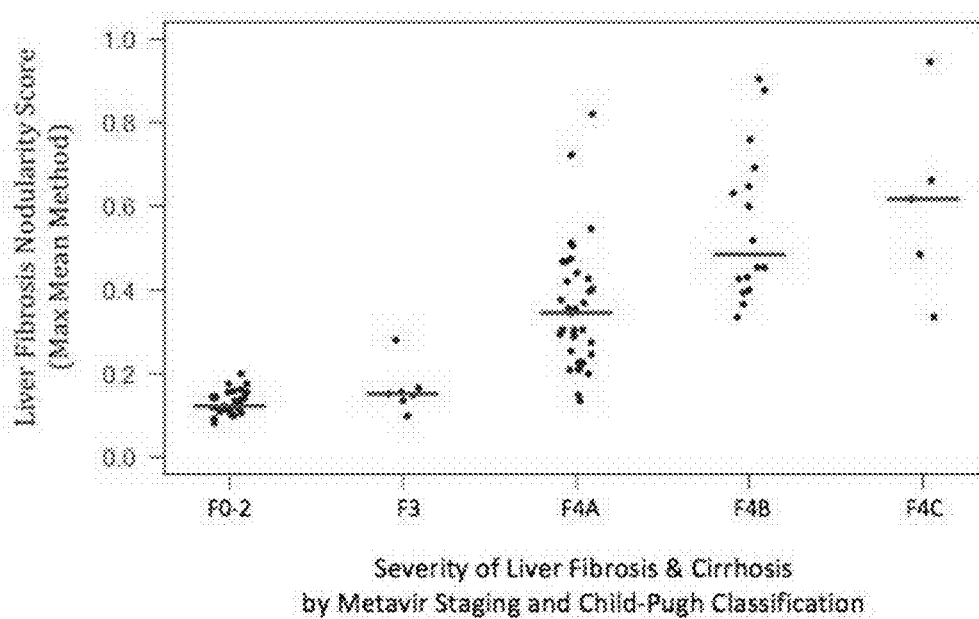
FIG. 4 shows how liver surface nodularity measurements by Max Mean Method and by Max SD Method are associated with the stage of HCV-induced liver fibrosis/cirrhosis (N=96).
Figure 4:
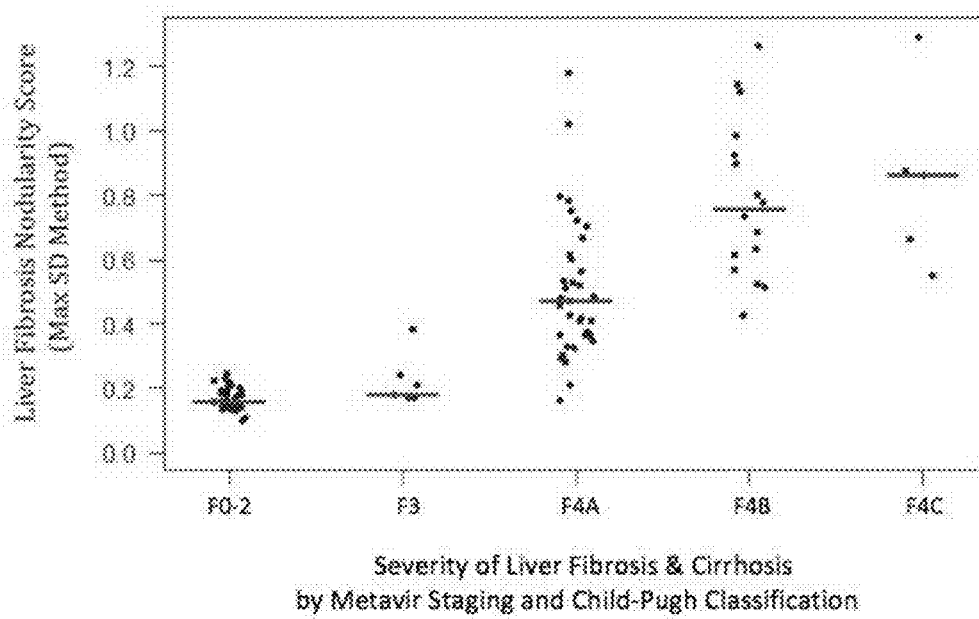

For CECT-thin imaging, the median liver surface nodularity scores by Max Mean Method and Max SD Method are depicted in FIG. 4. The bars in FIG. 4 represent the median liver surface nodularity scores for the respective groups of patients. The liver surface nodularity scores, by either method, were substantially higher in cirrhotics than noncirrhotics, and the scores in cirrhotics progressively increased with higher Child-Pugh classification. The area under the receiver operating characteristic curve (AUC) for differentiating noncirrhotic (F0-F3) from cirrhotic (F4A-F4C) was 0.982 for Max Mean Method and 0.982 for Max SD Method. For CECT-thin imaging, median liver surface nodularity scores by Max SD Method were as follows: F0-F2=1.59 (N=33), F3=1.78 (N=7), F4A=4.71 (N=35), F4B=7.58 (N=16), F4C=8.65 (N=5). The overall trend was that liver surface nodularity scores by either liver surface nodularity scoring method and for all imaging methods increased with progressively higher stage liver disease.

Figure 5:
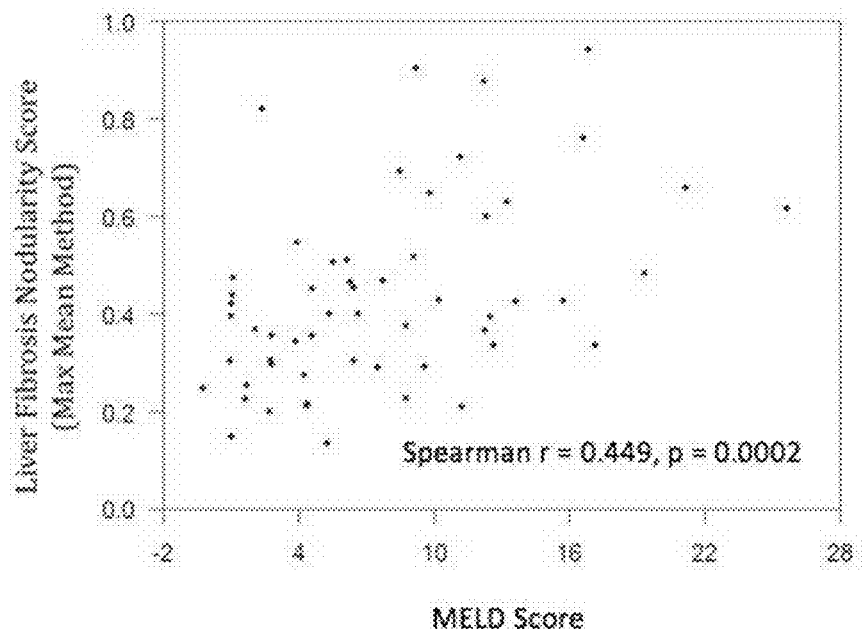
FIG. 5 shows how liver surface nodularity scores are associated with MELD and Child-Pugh scores in patients with HCV-induced cirrhosis (N=56).
Figure 5:
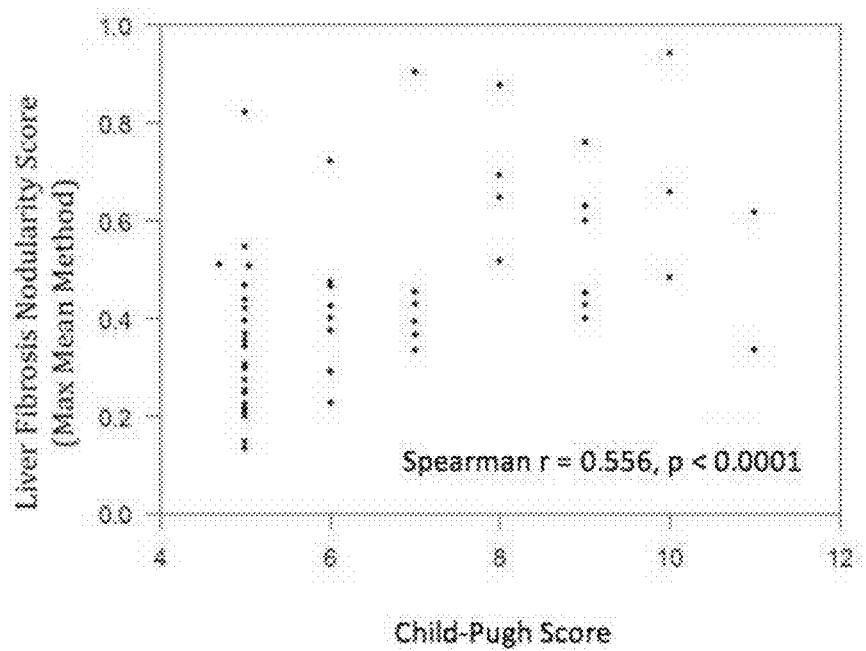

The AUC for liver surface nodularity scores by Max SD Method for differentiating cirrhotic (N=56) from non-cirrhotic (N=40) livers was 0.976, 0.977, 0.982, and 0.977 for NCCT-thin, NCCT-thick, CECT-thin, and CECT-thick imaging, respectively. Each individual's CECT-thin imaging median liver surface nodularity scores by Max SD Method were associated with MELD scores (Spearman correlation=0.476, P=0.0002) and Child-Pugh scores (Spearman correlation=0.563, P<0.0001) and are depicted in FIG. 5. The overall trend was a moderate positive correlation of liver surface nodularity scores with both MELD and Child-Pugh scores. Liver surface nodularity scores increased with higher MELD scores and higher Child-Pugh scores. Results were nearly identical for liver surface nodularity score by Max Mean Method. We concluded that liver surface nodularity scores on routine CT images are highly accurate for differentiating cirrhotic from non-cirrhotic livers.

The association of liver surface nodularity scores (by Max Mean Method and by Max SD Method) in combination with other imaging and laboratory variables on the stage of HCV-induced liver disease was evaluated in logistic regression models. Besides nodularity score, baseline measurements of platelets and liver volume (LLSV:TLV ratio) were identified as predictors of the stage of liver disease. We constructed a series of logistic regression models used for differentiating F2-F4C from F0-1, F3-F4C from F0-F2, and F4A-F4C from F0-F3. Let p(x) be the probability of having disease in advanced stage for given covariate values x. Let NS, PLT and LV denote liver surface nodularity score, platelets level and LLSV:TLV ratio, respectively. The logistic regression model can be mathematically presented as $$\log it[p(NS,PLT,LV)] = \beta_0 + \beta_1 NS + \beta_2 PLT + \beta_3 LV,$$

where $\log it(z) = \ln[z/(1-z)]$. The odds ratios of the three variables in individual logistic regression models are presented in Table 1. Let $\hat{\beta}_0$, $\hat{\beta}_1$, $\hat{\beta}_2$ and $\hat{\beta}_3$ be the maximum likelihood estimates of the regression coefficients. The risk scores for all patients were computed by the formula, $$\text{risk score} = \hat{\beta}_0 + \hat{\beta}_1 NS + \hat{\beta}_2 PLT + \hat{\beta}_3 LV.$$

The AUC for each set of risk scores indicates the power of the underlying model to discriminate individuals involved in the study (see Table 1). The AUC for differentiating F2-F4C from F0-F1 was 0.958 by Max Mean Method and 0.961 by Max SD Method. The AUC for differentiating F3-F4C from F0-F2 was 0.966 by Max Mean Method and 0.974 by Max SD Method. The AUC for differentiating F4A-F4C from F0-F3 was 0.997 by Max Mean Method and 0.997 by Max SD Method. Though in univariate analysis the nodularity scores alone had very high discriminating power, it was useful to explore significant imaging and laboratory variables. These variables have the potential to greatly improve the accuracy of classification in lower stage liver disease.

TABLE 1

Association of liver surface nodularity scores, liver volume and laboratory values with the stage of HCV-induced liver disease.

| Variable | Max Mean Method | | | | Max SD Method | | | |
|---|---|---|---|---|---|---|---|---|
| | OR | 95% CI | p value | AUC | OR | 95% CI | p value | AUC |
| Logistic regression and AUC values for differentiating F2-F4C from F0-F1 | | | | | | | | |
| Nodularity Score | 22.67 | 2.16-238.2 | 0.0093 | 0.958 | 9.33 | 1.75-79.85 | 0.0090 | 0.961 |
| Platelets | 0.50 | 0.67-0.92 | 0.0258 | | 0.49 | 0.26-0.92 | 0.0272 | |
| LLSV:TLV ratio | 1.24 | 0.55-2.80 | 0.6090 | | 1.21 | 0.53-2.78 | 0.6566 | |
| Logistic regression and AUC values for differentiating F3-F4C from F0-F2 | | | | | | | | |
| Nodularity Score | 30.15 | 2.24-406.3 | 0.0103 | 0.966 | 15.62 | 1.69-144.6 | 0.0155 | 0.974 |
| Platelets | 0.48 | 0.24-0.92 | 0.0270 | | 0.46 | 0.22-0.94 | 0.0324 | |
| LLSV:TLV ratio | 1.62 | 0.65-4.04 | 0.3013 | | 1.64 | 0.58-4.67 | 0.3535 | |

TABLE 1-continued

Association of liver surface nodularity scores, liver volume and laboratory values with the stage of HCV-induced liver disease.

| | Max Mean Method | | | | Max SD Method | | | |
|---|---|---|---|---|---|---|---|---|
| Variable | OR | 95% CI | p value | AUC | OR | 95% CI | p value | AUC |
| Logistic regression and AUC values for differentiating F4A-F4C from F0-F3 | | | | | | | | |
| Nodularity Score | 868.0 | 2.20->1000 | 0.0265 | 0.997 | 74.0 | 1.54->1000 | 0.0295 | 0.997 |
| Platelets | 0.08 | 0.01-0.91 | 0.0414 | | 0.10 | 0.01-1.00 | 0.0497 | |
| LLSV:TLV ratio | 21.8 | 1.12-425.7 | 0.0416 | | 19.1 | 0.97-374.8 | 0.0522 | |

Abbreviations:
OR, odds ratio;
CI, confidence interval;
AUC, area under the receiver operating characteristic curve.
OR's represent the effects for 0.1 unit increase in liver surface nodularity score, 50 unit increase in platelets, and 0.05 unit increase in LLSV:TLV ratio.

The following references are incorporated herein by reference in their entirety:
1. Schuppan D and Afdhal N H. Liver Cirrhosis. Lancet 2008; 371:838-51.
2. National Center for Health Statistics. US Department of Health and Human Services, Centers for Disease Control and Prevention; Hyattsville, Md.: 2005. Series 13.
3. Barsic N, Lerotic I, Smircic-Duvnjak L, Tomasic V, Duvnjak M. Overview and developments in noninvasive diagnosis of nonalcoholic fatty liver disease. Word J Gastroenterol. 2012; 18:3945-54.
4. Regev A, Berho M, Jeffers L J, et al. Sampling error and intraobserver variation in liver biopsy in patients with chronic HCV infection. Am J Gastroenterol 2002; 97:2614-18.
5. Abdi W, Millan J C, Mezey E. Sampling variability on percutaneous liver biopsy. Arch Intern Med 1979; 139: 667-69.
6. 7. Bedossa P, Dargere D, Paradis V. Sampling variability of liver fibrosis in chronic hepatitis C. Hepatology 2003; 38:1449-57.
7. Bedossa P and Poynard T. An algorithm for the grading of activity in chronic hepatitis C. Hepatology. 1996; 290: 289-93.
8. Infante-Rivard C, Esnaola S, Villeneuve J P. Clinical and statistical validity of conventional prognostic factors in predicting short-term survival among cirrhotics. Hepatology 1987; 7:660-64.
9. Wiesner R, Edwards E, Freeman R, et al. Model for end-stage liver disease (MELD) and allocation of donor livers. Gastroenterology 2003; 124:91-96.
10. Ito K, Mitchell D G, Hann H W, et al. Viral-induced cirrhosis: Grading of severity using MR imaging. AJR Am J Roentgenol 1999; 173:591-96.
11. Frulio N, Trillaud H. Ultrasound elastography in liver. Diagn Intery Imaging. 2013; 94:515-34.
12. Choong C C, Venkatesh S K, Siew E P. Accuracy of routine clinical ultrasound for staging of liver fibrosis. J Clin Imaging Sci. 2012; 2-58.
13. Ong T Z, Tan H J. Ultrasonography is not reliable in diagnosing liver cirrhosis in clinical practice. Singapore Med J. 2003; 44:293-5.
14. Cobbold J F L, Patel D, Taylor-Robinson S D. Assessment of inflammation and fibrosis in non-alcoholic fatty liver disease by imaging-based techniques. J Gastroentol Hepatol. 2012; 27:1281-92.
15. Rustogi R, Horowitz J, Harmath C, et al. Accuracy of MR elastography and anatomic MR imaging features in the diagnosis of severe hepatic fibrosis and cirrhosis. J Magn Reson Imaging. 2012 June; 35(6):1356-64.
16. Keedy A, Westphalen A C, Qayyum A, et al. Diagnosis of cirrhosis by spiral computed tomography: a case-control study with feature analysis and assessment of interobserver agreement. J Computed Assist Tomogr. 2008; 32:198-203.
17. Castera L. Noninvasive methods to assess liver disease in patients with hepatitis B or C. Gastroenterology. 2012; 142:1293-302.
18. Chou R and Wasson N. Blood tests to diagnose fibrosis or cirrhosis in patients with chronic hepatitis C virus infection. Ann Intern Med. 2013; 158:807-20.
19. Ferral H, Male R, Cardiel M, et al. Cirrhosis: Diagnosis by liver surface analysis with high-frequency ultrasound. Abdom Imaging. 1992; 17:74-78.

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

I claim:

1. A computer-implemented method for obtaining data to assist in ascertaining stage severity of at least one of liver fibrosis or cirrhosis in a subject, the method comprising:
   receiving one or more medical images of a liver, the one or more medical images comprising at least one of computed tomography or magnetic resonance medical images;
   determining a detected liver boundary for each of a plurality of liver sections from the one or more medical images;
   calculating a liver surface nodularity score for each of a plurality of liver sections from the one or more medical images, wherein calculating the liver surface nodularity score for each of the plurality of liver sections comprises:
   fitting a smooth spline to the detected liver boundary for each of the plurality of liver sections;
   determining a distance between the detected liver boundary and the smooth spline at each pixel of the detected liver boundary; and applying a mathematical adjustment to the determined distance, the mathematical adjustment comprising one or more of an exponential amplification of the distance or a log transformation of the distance; and based on at least a mean or a median liver surface nodularity score calculated from the liver surface nodularity score for each of the plurality of liver sections, determining a stage severity of at least one of liver fibrosis or cirrhosis.

2. The method of claim 1, wherein the liver surface nodularity score is expressed in continuous units, with a higher nodularity score being associated with a higher stage of liver fibrosis or cirrhosis.

3. The method of claim 2, wherein the step of fitting the smooth spline to the detected liver boundary is performed such that the smooth spline mimics a smooth liver surface.

4. The method of claim 1, further comprising the steps of:
identifying varices on the one or more medical images or from an endoscopy report; and
using a presence or absence of varices to additionally inform the step of determining the stage severity of at least one of liver fibrosis or cirrhosis.

5. The method of claim 1, further comprising the steps of:
observing at least one of an age of the liver or a body mass index of a body to which the liver belongs; and
mathematically combining said observation with said liver surface nodularity score when determining the stage severity of at least one of liver fibrosis or cirrhosis.

6. The method of claim 1, further comprising the steps of:
receiving a physical measure of liver stiffness, the physical measure of liver stiffness being obtained from one of an imaging measurement device or a clinical measurement device; and
mathematically combining the physical measure of liver stiffness with said liver surface nodularity score when determining the stage severity of at least one of liver fibrosis stage or cirrhosis.

7. The method of claim 6, wherein obtaining a physical measure of liver stiffness step includes measuring a quantitative liver stiffness value by at least one of transient elastography (TE), ultrasound shear wave elastography (SWE), ultrasound acoustic radiation force elastography (ARFI), ultrasound strain (static or compression) elastography, or magnetic resonance elastography (MRE).

8. The method of claim 1, further comprising automatically trimming the detected liver boundary by 2 mm.

9. The method of claim 8, further comprising measuring and recording a length of the detected liver boundary.

10. The method of claim 9, wherein a sum of lengths of the detected liver boundaries from the plurality of liver sections is greater than 10 cm.

11. The method of claim 1, further comprising generating an overall irregularity for each detected liver boundary by combining the distance between the detected liver boundary and the smooth spline at each pixel of the detected liver boundary, the overall irregularity corresponding to a combination of one or more outward projections and inward retractions of the detected liver boundary along the corresponding smooth spline.

12. The method of claim 1, wherein the smooth spline comprises a contour fit of at least 20 mm.

13. A computer-implemented method for obtaining data to assist in ascertaining stage severity of at least one of liver fibrosis or cirrhosis in a subject, the method comprising:

receiving one or more medical images of a liver, the one or more medical images comprising at least one of computed tomography or magnetic resonance medical images;

determining a detected liver boundary for each of a plurality of liver sections from the one or more medical images, the detected liver boundary comprising a length;

calculating a liver surface nodularity score for each of a plurality of liver sections from the one or more medical images, wherein calculating the liver surface nodularity score for each of the plurality of liver sections comprises:

fitting a smooth spline to the detected liver boundary for each of the plurality of liver sections;

determining a distance between the detected liver boundary and the smooth spline at a plurality of points along the length of the detected liver boundary; and applying a mathematical adjustment to the determined distance at the plurality of points, the mathematical adjustment comprising a mean of the determined distance at the plurality of points along the length of the detected liver boundary; and based on at least a mean or a median liver surface nodularity score calculated from the liver surface nodularity score for each of the plurality of liver sections, determining a stage severity of at least one of liver fibrosis or cirrhosis.

14. The method of claim 13, wherein the liver surface nodularity score is expressed in continuous units, with a higher nodularity score being associated with a higher stage of liver fibrosis or cirrhosis.

15. The method of claim 13, further comprising the steps of:
identifying varices on the one or more medical images or from an endoscopy report; and
using a presence or absence of varices to additionally inform the step of determining the stage severity of at least one of liver fibrosis or cirrhosis.

16. The method of claim 13, further comprising the steps of:
receiving a physical measure of liver stiffness, the physical measure of liver stiffness being obtained from one of an imaging measurement device or a clinical measurement device; and
mathematically combining the physical measure of liver stiffness with said liver surface nodularity score when determining the stage severity of at least one of liver fibrosis stage or cirrhosis.

17. The method of claim 16, wherein obtaining a physical measure of liver stiffness step includes measuring a quantitative liver stiffness value by at least one of transient elastography (TE), ultrasound shear wave elastography (SWE), ultrasound acoustic radiation force elastography (ARFI), ultrasound strain (static or compression) elastography, or magnetic resonance elastography (MRE).

18. The method of claim 13, further comprising automatically trimming the length of the detected liver boundary by 2 mm.

19. The method of claim 18, wherein a sum of lengths of the detected liver boundaries from the plurality of liver sections is greater than 10 cm.

20. The method of claim 13, wherein the smooth spline comprises a contour fit of at least 20 mm.

* * * * *